US00PP17323P2

(12) United States Plant Patent
Meilland

(10) Patent No.: US PP17,323 P2
(45) Date of Patent: Dec. 26, 2006

(54) FLORIBUNDA ROSE PLANT NAMED 'MEIFRICHTY'

(50) Latin Name: *Rosa hybrida*
Varietal Denomination: Meifrichty

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 22 days.

(21) Appl. No.: 11/195,698

(22) Filed: Aug. 3, 2005

(51) Int. Cl.
*A01H 5/00* (2006.01)

(52) U.S. Cl. ..... Plt./150

(58) Field of Classification Search ..... Plt./150
See application file for complete search history.

*Primary Examiner*—Kent Bell
*Assistant Examiner*—June Hwu
(74) *Attorney, Agent, or Firm*—Buchanan Ingersoll & Rooney PC

(57) ABSTRACT

A new and distinct variety of Floribunda rose plant is provided which abundantly forms on a nearly continuous basis attractive Cardinal red blossoms having five petals and a yellow eye. The plant exhibits strong vegetation, a low and compact growth habit, very dense medium green foliage with a glossy aspect, and good tolerance to Oidium. The attractive medium green glossy foliage contrasts nicely with the red blossom coloration. The new variety is particularly well suited for growing as attractive ornamentation in parks and gardens.

1 Drawing Sheet

Figures 1, 2, 3, 4, 5, 6, 7, 8, 9, 10, 11, 12, 13, 14, 15, 16:
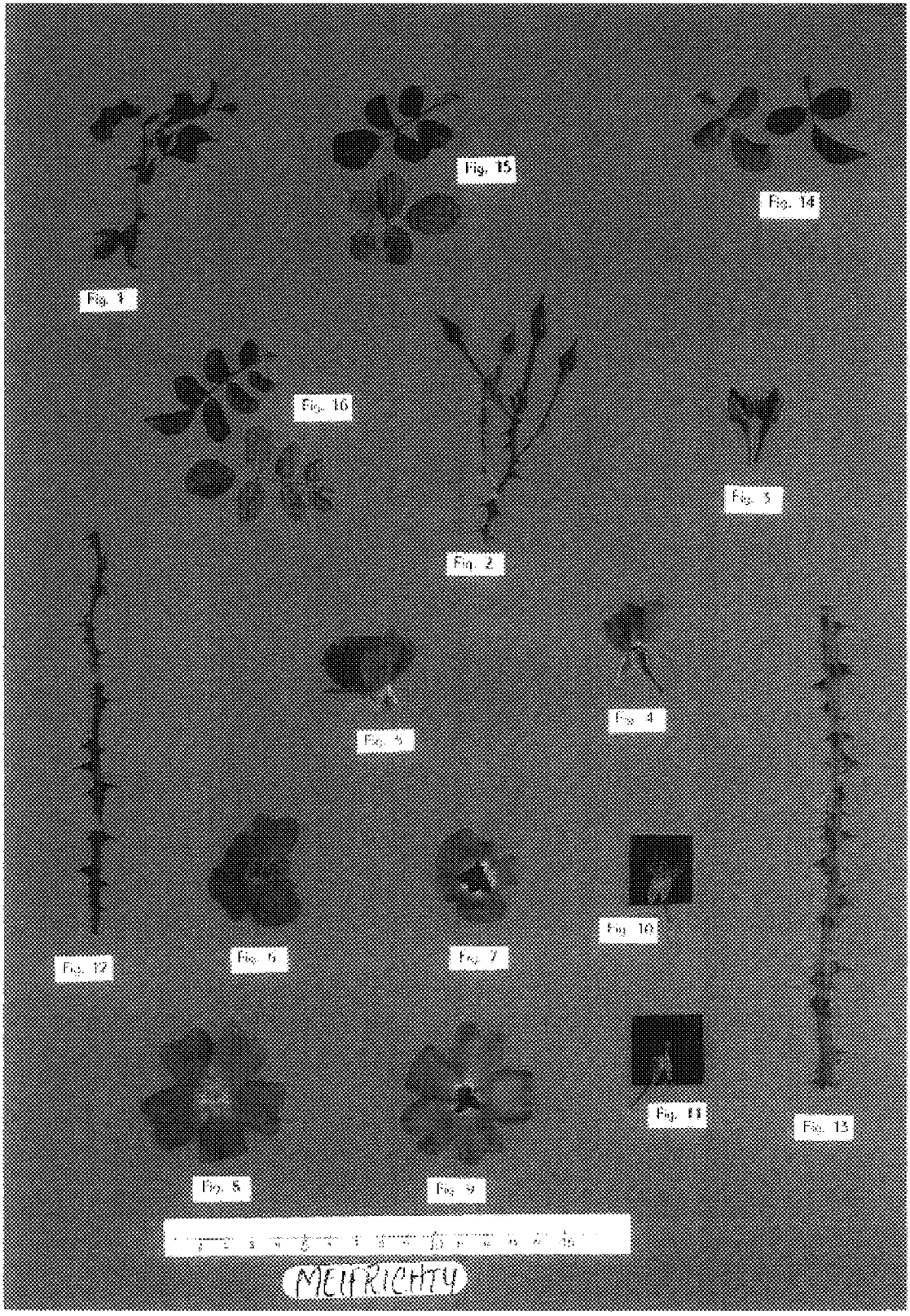

Botanical/commercial classification: *Rosa hybrida*/Floribunda Rose Plant.
Varietal denomination: cv. Meifrichty.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) was the product of the cross of the 'Meineble' variety (U.S. Plant Pat. No. 7,116) and the 'Meipoque' variety (U.S. Plant Pat. No. 5,956). The male parent (i.e., the pollen parent) was the 'Korimro' variety (non-patented in the United States). The parentage of the new variety can be summarized as follows: ('Meineble'× 'Meipoque')×'Korimro'.

The seeds resulting from the above pollination were sown and small plants were obtained which were physically and biologically different from each other. Selective study resulted in the identification of a single plant of the new variety.

It was found that the new Floribunda rose plant of the present invention:

(a) exhibits a low and compact growth habit, (b) abundantly forms on a nearly continuous basis attractive Cardinal red blossoms having five petals and a yellow eye, (c) forms very dense medium green foliage having a glossy aspect that contrasts well with the blossom coloration, and (d) is particularly well suited for growing as attractive ornamentation in parks and gardens.

The disease tolerance is very good with respect to Oidium, and the blossom coloration is relatively stable.

The new variety well meets the needs of the horticultural industry and can be grown to advantage in the landscape where attractive ornamentation is desired.

The new variety can be readily distinguished from its ancestors. For instance, the 'Meineble' variety displays a considerably taller growth habit. The 'Meipoque' and 'Korimro' varieties each form blossoms having a dissimilar pink coloration.

Additionally, the new variety can be readily distinguished from the 'Eye Paint' (U.S. Plant Pat. No. 3,985) and 'Meirumour' (U.S. Plant Pat. No. 9,251) varieties. Each of these comparative varieties displays a significantly taller growth habit.

The new variety has been found to undergo asexual propagation in France by a number of routes, including budding, grafting, and the use of cuttings. Asexual propagation by the above-mentioned techiques in France has shown that the characteristics of the new variety are stable and are strictly transmissible by such asexual propagation from one generation to another.

The new variety has been named 'Meifrichty'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during September while budded on *Rosa froebelli* understock and growing outdoors at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates specimens of two floral buds at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates specimens of leaves with three leaflets—plan view—upper surface (right) and—under surface (left);

FIG. 15—illustrates specimens of leaves with five leaflets—plan view—upper surface (top) and—under surface (bottom); and FIG. 16—illustrates specimens of leaves with seven leaflets—plan view—upper surface (top) and—under surface (bottom).

DETAILED DESCRIPTION

The chart used in the identification of the colors is that of The Royal Horticultural Society (R.H.S. Colour Chart). The description is based on the observation of one year-old plants during September while budded on *Rosa froebelli* understock and growing outdoors at Le Cannet des Maures, Var, France.

Class: Floribunda.

Plant:

*Height.*—Approximately 40 to 50 cm on at average the end of the growing season.

*Width.*—Approximately 40 to 50 cm on average at the end of the growing season.

*Habit.*—Bushy.

Branches:

*Color.*—Young stems: near Yellow-Green Group 146C. Adult wood: near Yellow-Green Group 146C.

*Texture.*—Young stems: smooth with thorns and prickles. Adult stems: smooth with thorns and prickles.

*Thorns.*—On young stems: Small prickles: Configuration: rather upright on the upper surface and slightly concave on the under surface with an oval base. Quantity: approximately 90 on average on a stem length of 10 cm. Length: Approximately 0.1 cm on average. Color: near Yellow Green Group 153B. Long prickles: Configuration: longish-pointed and curved downwards on the upper surface and slightly concave on the under surface with an oval base. Quantity: approximately 22 on average on a stem length of 10 cm. Length: approximately 0.3 to 0.5 cm on average. Color: near Red Group 53B. On adult stems: Small prickles: Configuration: rather upright on the upper surface and slightly concave on the under surface with an oval base. Quantity: approximately 41 on average on a stem length of 10 cm. Length: approximately 0.2 cm on average. Color: near Yellow-Green Group 153B. Long prickles: Configuration: rather upright on the upper surface and slightly concave on the under surface. Quantity: approximately 14 on average on a stem length of 10 cm. Length: approximately 1 cm on average. Color: near Yellow-Green Group 153B suffused with near Greyed-Red Group 179A.

Leaves:

*Size.*—A seven-leaflet including the petiole commonly is approximately 8.9 cm in length on average, and is approximately 4.8 cm in width on average.

*Stipules.*—Smooth texture, adnate, pectinate, rather broad, approximately 1 cm in length on average, approximately 0.4 cm in width on average, near Green Group 138B and 138C on the upper surface, and near Green Group 138B on the under surface.

*Petioles.*—Upper surface: smooth, non-glandular and near Green Group 138B in coloration. Under surface: bear a few prickles, and near Green Group 138B in coloration. Length: approximately 1.8 cm for the terminal leaflet.

*Rachis.*—Upper surface: smooth, and near Green Group 138B suffused with Greyed-Red Group 179A in coloration. Under surface: bear a few prickles, and near Green Group 138B in coloration.

*Leaflets.*—Number: 3, 5 and 7 (most frequent). Shape: generally oval with an obtuse base and a pointed tip. Size: the terminal leaflets commonly are approximately 4 cm in length and approximately 2.5 cm in width on average. Serration: small and single (as illustrated). Texture: physically firm and thick. General appearance: very dense, medium green, and glossy. Color (young foliage): Upper surface: near Yellow-Green Group 146A. Under surface: near Yellow-Green Group 146B. Color (adult foliage): Upper surface: near Green Group 137A. Under surface: near Green Group 138B.

Inflorescence:

*Number of flowers.*—Commonly two to five blossoms per stem.

*Peduncle.*—Glandular, near Yellow-Green Group 144C suffused with Greyed-Red Group 179A, approximately 1.7 cm in length, of sufficient strength to well sustain the flower and approximately 0.2 cm in diameter.

*Sepals.*—Upper surface: smooth and near Yellow-Green Group 148C in coloration. Under surface: smooth and near Yellow-Green Group 144B and 144C in coloration. Configuration: lacking in a long extended tip, incurved at the base, approximately 1.3 cm in length on average, and approximately 0.5 cm in width on average at the widest point.

*Bud.*—Shape: conical. Size: small. Length: approximately 1 to 1.2 cm on average. Width: approximately 0.7 cm on average at the widest point. Color: Upper surface: near Red Group 46A suffused with Red Group 53A as the calyx breaks. Under surface: near Red Group 46A suffused with Red Group 53A as the calyx breaks. Basal spot: small, on both surfaces, and near Yellow Group 2C as the calyx breaks.

*Flower.*—Shape: flat, cup-shaped. Diameter: approximately 4 to 4.5 cm on average. Color (in the course of opening): Upper surface: Cardinal Red, near Red Group 53C and widely suffused with Red Group 45A. Under surface: Cardinal Red, near Red Group 53C and widely suffused with Red Group 45A. Basal petal spot: near Yellow Group 2C on both surfaces. Color (when fully open): Upper surface: Cardinal Red, near Red Group 53C and widely suffused with Red Group 45A. Under surface: Cardinal Red, near Red Group 53C and widely suffused with Red Group 45A. Basal petal spot: Yellow Group 2C. Color stability: very slight discoloration with age. Fragrance: none. Lasting quality: the blossoms commonly last approximately two weeks on the plant on average. The longevity of the blossoms when cut and placed in vase has not been evaluated since the variety is primarily intended for providing ornamentation in the landscape. Petal number: five under normal growing conditions. Petal shape: cuneiform base with a reflexed tip. Petal texture: consistent and somewhat firm. Petal apex: reflected. Petal base: cuneiform. Petal length: approximately 2.3 cm on average. Petal width: approximately 2 cm on average. Petal arrangement: imbricated; and without petaloids. Petal drop: good with the petals commonly detaching cleanly. Stamen number: approximately 83 on average. Anthers: regularly arranged around the styles, approximately 0.1 cm in size on average, and near Yellow-Orange Group 15A in coloration. Pollen: present and near Yellow-Orange Group 15A in coloration. Filaments: approximately 0.3 cm in length on average and near Yellow Group 2C in coloration. Pistils: approximately 13 on average. Stigmas: approximately 0.1 cm in size on average and near Yellow-Green Group 154C in coloration. Styles: approximately 0.3 cm in length, on average, and near Yellow-Green Group 154C in coloration. Receptacle: smooth, pitcher-shaped in longitudinal section, approximately 0.6 cm in length on average, approximately 0.3 cm in width on average at the widest point, and near Yellow-Green Group 144C in coloration. Hips: generally rounded, approximately 1 cm in size on average, and near Yellow-Green Group 144C in coloration.

Development:

*Vegetation.*—Strong.

*Blooming.*—Very abundant and nearly continuous.

*Resistance to diseases.*—Very good tolerance with respect to Oidium.

*Aptitude to bear fruit.*—Typical.

*Resistance to cold.*—U.S.D.A. Hardiness Zone No. 6A, and has never shown frost damage under the winter conditions of Western Europe.

*Resistance to heat.*—grows well in Provence of France at temperatures of 100° F.

I claim:

1. A new and distinct variety of Floribunda rose plant characterized by the following combination of characteristics:

(a) exhibits low and compact growth habit, (b) abundantly forms on a nearly continuous basis attractive Cardinal red blossoms having five petals and a yellow eye, (c) forms very dense medium green foliage having a glossy aspect that contrasts well with the blossom coloration, and (d) is particularly well suited for growing as attractive ornamentation in parks and gardens;

substantially as herein shown and described.

* * * * *

MEIFRICHTY